(12) United States Patent
Chong et al.

(10) Patent No.: US 6,525,089 B1
(45) Date of Patent: Feb. 25, 2003

(54) PHARMACEUTICAL COMPOSITION CONTAINING DECURSIN

(75) Inventors: Se Young Chong, Seoul (KR); Ik Hwan Kim, Seoul (KR); Kyung Seop Ahn, Daejeon (KR); Sang Ki Kim, Seoul (KR)

(73) Assignee: Binex Co., Ltd. (KR)

( * ) Notice: Subject to any disclaimer, the term of this patent is extended or adjusted under 35 U.S.C. 154(b) by 0 days.

(21) Appl. No.: 09/807,858

(22) PCT Filed: Oct. 21, 1999

(86) PCT No.: PCT/KR99/00632

§ 371 (c)(1),
(2), (4) Date: Apr. 19, 2001

(87) PCT Pub. No.: WO00/23074

PCT Pub. Date: Apr. 27, 2000

(30) Foreign Application Priority Data

Oct. 22, 1998 (KR) .............................................. 98-44339
Oct. 22, 1998 (KR) .............................................. 98-44340

(51) Int. Cl.⁷ ............................................... A61K 31/37

(52) U.S. Cl. ........................ 514/455; 514/256; 514/269; 514/866; 514/908; 514/922

(58) Field of Search ................................ 514/455, 256, 514/269, 866, 908, 922

(56) References Cited

PUBLICATIONS

Ahn et al, "Decursin: A Cytotoxic Agent and Protein Kinase C Activator From The Root of Angelica Gigas", Planta Med. 62, pp. 7–9 (1996).*

Itokawa et al, "Cytotoxic Coumarins From Roots of Angelica Gigas", Natural Medicines 48(4), 334–335 (1994).*

Lippincott's Illustrated Reviews, Pharmacology, Second Edition, pp. 395–396 (1997).*

\* cited by examiner

Primary Examiner—Frederick Krass
(74) Attorney, Agent, or Firm—Candice J. Clement, Esq.; Heslin Rothenberg Farley & Mesiti, P.C.

(57) ABSTRACT

A pharmaceutical composition comprising decursin and its uses as a nephrotoxicity inhibitor, an antineoplastic agent, an antidiabetic agent, and as a cancer-cell differentiation induction agent are disclosed.

11 Claims, No Drawings

PHARMACEUTICAL COMPOSITION CONTAINING DECURSIN

This application is a 35 USC §371 filing of PCT/KR99/00632, filed Oct. 21, 1999 and claims priority from KR 1998-44339 and KR 1998-44340, both filed Oct. 22, 1998. The entire disclosures of the earlier applications are incorporated herein by reference.

TECHNICAL FIELD

The present invention relates to a pharmaceutical composition containing decursin and its pharmaceutically acceptable carrier.

BACKGROUND ART

As a great number of the pharmaceutical compositions used in the prevention or treatment of various diseases have a variety of toxicities including nephrotoxicity (i.e., toxicity on the kidney), due care should be exercised in their clinical use. In particular, when using antineoplastic or antibiotic composition, since its side effect such as nephrotoxicity is very serious, its clinical use has been extremely restricted. For example, cisplatin is an antineoplastic agent used in the treatment of various tumors of the testis, esophagus, stomach, bladder, prostate, lung, neck of uterus and osteosarcoma, notably of genital tumors. However, its serious toxicities on the kidney, ears, gastro-intestine and bone marrow have been reported including allergies. Among these, nephrotoxicity becomes so severe as to lead renal failure with high dose of cisplatin for a long-term period, and thus clinical use of cisplatin has been extensively restricted. Under this situation, it is clinically important to reduce the toxicity of cisplatin on the bone marrow, gastrointestinal tract, and particularly on the kidney in the treatment of various cancers using cisplatin.

Intensive researches have been focused on the alleviation of nephrotoxicity associated with the use of cisplatin. The conventional methods designed to reduce the nephrotoxicity are as follows: One is to synthesize platinum derivatives less toxic than cisplatin; one example being carboplatin. However, its toxicity on the bone marrow is very severe even though its nephrotoxicity is less than cisplatin. Another is to facilitate the excretion of drug for reducing the toxicity. To this end, mannitol or hypertonic saline solution is concurrently used. However, this method may shorten the half-life of cisplatin, resulting in decreasing the antineoplastic effect. A third is to administer an antineoplastic agent together with antidotes via a two-route chemotherapy (TRC) so as to reduce the toxicities of cisplatin. To this end, bismuthsubnitrate or selenium is concurrently used. Ho,A/ever, this method may cause some adverse effect such as accumulation of heavy metals in the body.

In the meantime, all of the normal cells in the human body are formed by proliferation to a certain extent and a subsequent differentiation as an indispensable process. It is believed that such proliferation and differentiation process are controlled at the genetic level. Unlike the normal cells, however, cancer cells consist of immature cells that freely proliferate without any differentiation, despite the fact that the cells are derived from normal tissue. As a result, cancer cells differ from normal cells in terms of metabolism, enzyme patterns and surface structure of cells (Raymond W. Ruddon, Cancer: A disease of abnormal differentiation, Cancer Biology, 2nd edition: 69, 1987).

The development mechanism of such undifferentiated cancer cells has yet to be reported. However, the main debate on the development of cancer cells has been centered on whether the differentiation-completed adult cells are dedifferentiated or the undifferentiated cells lose their differentiation capacity. According to the report up to the present, the transformation into cancel cells occurs only in the normal cells capable of proliferation; while the differentiation of cells in which its short-term fate to a certain path way is already programmed is irreversible, the terminal differentiation itself is reversible (D. Yaffe, Cellular aspects of muscle differentiation in vitro. Current Topics in Developmental Biology, 4:39, 1969).

Pierce et al. reported that normal tissue stem cells with renewal capacity are origins of malignant tumor (G. B. Pierce, Differentiation of normal and malignant cells, Fed. Proc.29: 1248, 1970). The stem cells coincide with the cancer cells in that they are products of undifferentiated cells with sustained proliferation capacity. However, recent studies revealed that the abnormality in cancer cell is not completely irreversible. The conventional method that is frequently applied to leukemia, hepatocyte and fibroblast cells, is to induce differentiation of cancer cells into the normal cells or their similar cells by way of differentiation induction agent (Alphonse Krystosek and Leo Sachs, Control of lysozyme induction in the differentiation of myeloid leukemia cells, Cell, 9:675:684, 1976; Shinichi Murao, M. Anne Gemmell, Michael F. Callaham, N. Leigh Anderson and Eliezer Huberman, Control of macrophage cell differentiation in human promyelocytic U-937 leukemia cells by 1,25-dihydroxy vitamin D3 and phorbol-12 myristate-13-acetate, Cancer Research, 43:4989–4996, 1983). Unlike the conventional antineoplastic agents based on the cytotoxic mechanism, this method is significant in that it is designed to treat the neoplastic tumors via new pathway. Moreover, some of the conventional antineoplastic agents are reported to have differentiation induction function at a concentration lower than cytotoxic concentration, which is very stimulating in that side effect of the antineoplastic agent can be alleviated by using at a very low concentration.

In fact, active vitamin A, which is known as a differentiation induction agent, is clinically employed to the treatment of acute promyelocytic leukemia (APL) where the combined therapy of multi-drug using daunomycin has been mainly conducted hitherto. According to the Journal of American Blood Association published on November 1988, it is reported that when a large dose of retinoic acid was administered to 22 APL patients, 96% of them were in complete remission. Thereafter, this method was adopted in many medical institutions in the United States, France, Japan, etc., and achieved an average remission rate of more than 80% with an average remission time of 29 days. In addition, there showed side effects including skin dryness and gastric disturbance, but their severity was milder than other antineoplastic agents. Thus, it can be said that the differentiation induction agent has been significantly recognized as a beneficial antineoplastic agent from the worldwide medical arena.

The therapeutic mode of action in conventional antineoplastic agents is related to the cytotoxicity to kill the rapid growing cancer cells via inhibition of DNA replication, reduction of intracellular metabolism and biosynthesis or generation of free radicals. Therefore, a very high dose of the agent has been required. In this case, adverse effects are expected in various organs where cell proliferation is fairly rapid such as bone marrow, as well as in the organs where the agent is metabolized and excreted such as gastrointestinal tract, liver, kidney and cardiovascular tissues. In fact, administration of such antineoplastic agent is much limited due to such severe side effects. Accordingly, there has been a strong need for the development of a novel antineoplastic agent with less toxicity, i.e., the agent with cancer-cell differentiation induction function.

Decursin is a natural product that was firstly isolated from *Angelica decursiva* (Fr. et Sav.) in Japan in 1966. It was reported in 1967 and 1969 that *Angelica gigas* Nakai contains a large amount of decursin (J. Pharm. Soc. Korea, 11: 22–26, 1967 and 13: 47–50, 1969). In addition, decursin was also isolated from the fruit of *Peucedanum terebinthaceum* (Fisher et Turcz) (Korea Pharmacology Journal 30(2): 73–78, 1986). As for the pharmacological effect of decursin, the present inventors discovered in 1993 that decursin has toxicity on various cell lines of uterine cancer, leukemia, hepatoma or large intestine cancer at concentration of more than 10 ppm (See Korean Patent Application No. 93-17935).

Disclosure of the Invention

Through intensive research for a long time, the present inventors discovered various use of decursin to complete the present invention.

An object of the present invention is to provide a nephrotoxicity inhibitor composition comprising decursin as an active ingredient and a pharmaceutically acceptable carrier.

Another object of the present invention is to provide an antineoplastic composition comprising decursin as a nephrotoxicity inhibitor, an antineoplastic agent and a pharmaceutically acceptable carrier.

A further object of the present invention is to provide an antidiabetic composition comprising decursin as a nephrotoxicity inhibitor, an antidiabetic agent and a pharmaceutically acceptable carrier.

A further object of the present invention is to provide a cancer-cell differentiation induction agent composition comprising decursin as an active ingredient and a pharmaceutically acceptable carrier.

The present invention relates to a pharmaceutical composition containing decursin.

According to the present invention, the pharmaceutical composition containing decursin as a nephrotoxicity inhibitor can effectively inhibit the nephrotoxicity associated with the pharmaceuticals. In particular, as can be seen in the following examples, decursin can effectively inhibit the nephrotoxicity of cisplatin, a representative antineoplastic agent, as well as that of alloxan, a representative diabetes-inducing material.

Therefore, the pharmaceutical composition of the present invention may be in the form of nephrotoxicity inhibitor composition containing decursin as an active ingredient.

Furthermore, the pharmaceutical composition of the present invention may be in the form of antineoplastic composition containing decursin as a nephrotoxicity inhibitor. In this case, 1~5 moles of decursin may be employed to 1 mole of antineoplastic agent, and the examples of antineoplastic agent may include cisplatin.

Furthermore, the pharmaceutical composition of the present invention may be in the form of antidiabetic composition containing decursin as a nephrotoxicity inhibitor. In this case, 0.2~10 moles of decursin may be employed to 1 mole of antidiabetic agent.

The dose of the composition containing decursin as a nephrotoxicity inhibitor may vary depending on its purposes; the composition may be administered at a dose of 1~500 mg per kg of body weight.

Although the mechanism of inhibiting nephrotoxicity by decursin has not been proved yet, it appears to be caused by the scavenger effect of decursin owing to its powerful antioxidation property. For example, the nephrotoxicity of cisplatin can be explained as a typical inflammation process, including that cisplatin, which is already distributed throughout the body, is absorbed in the proximal renal tubules of kidney while being rapidly excreted, then neutrophils are induced and stimulated by chemotaxis and finally the surrounding normal tissue is damaged by the oxygen radicals secreted from the neutrophils. Therefore, antioxidants actina as a scavenger for free radicals can be thought to alleviate the nephrotoxicity of cisplatin. For this purpose, however, the following requirements should be met. Firstly, the antioxidants should be adequately distributed in the body during the above process. Secondly, the antioxidants should not be the bio-substances that are produced in the body and needed by the whole body tissues including kidney so that cancer cells cannot absorb the antioxidants and thus protect themselves. Thirdly, the antioxidants should not be easily metabolized to be inactive or have a strong affinity to the liver, which may result in delaying the distribution of the antioxidants in the kidney or decreasing the amount to be distributed. In other words, it is thought that decursin has the above three requirements so as to effectively act as a scavenger of free radical and thus effectively inhibit the nephrotoxicity.

Next, the pharmaceutical composition of the present invention containing decursin as a cancer-cell differentiation induction agent may vary in its dose depending on the purpose; the pharmaceutical composition may be administered at a dose of 1~300 mg per kg of body weight.

The composition of the present invention comprising decursin as an active ingredient can effectively induce the cancer-cell differentiation. In particular, as can be seen in the following examples, decursin can effectively induce the differentiation of human leukemia cells. In other words, the composition of the present invention can be used as a novel antineoplastic composition since decursin can induce the differentiation of the cancer-cell, particularly of human leukemia cell, at much lower concentration than cytotoxicity-producing concentration.

The pharmaceutical composition of the present invention containing decursin may be formulated in various dosage forms using pharmaceutically acceptable carriers, excipients and/or additives. More specifically, the pharmaceutical composition of the present invention may include excipients such as lactose, starch, etc., lubricants such as magnesium stearate, emulsifiers, suspension agents and isotonic agents, and if desired, sweetening agents and/or flavors. Furthermore, the pharmaceutical composition of the present invention may be formulated in oral or peripheral dosage form; the oral dosage forms include tablet, capsule and liquid, while the peripheral dosage forms include intravenous, intraperitoneal, and subcutaneous injection.

The present invention is explained in detail in the following examples but is not limited by those examples.

EXAMPLE 1

The Effect of Decursin on Alleviating Nephrotoxicity Associated with the use of Cisplatin To determine the inhibitory effect of decursin on the side effects associated with the use of cisplatin, such as weight loss, nephrotoxicity and hepatotoxicity, a mixture of cisplatin and decursin was administered to normal SD rats while changing the dose amount, dose period and dose frequency. The detailed test methods were summarized hereinafter.

BUN (blood urea nitrogen) and creatinine as a marker of nephrotoxicity in the blood, sGPT as a marker of hepatotoxicity, occult blood in the urine, bilirubin, urobilinogen, ketone, protein, nitrite, glucose, pH and specific gravity were determined as follows.

(1) Measurement of BUN

BUN value was measured using the BUN measurement kit (Youngdong Pharm. Co. Ltd., Korea) in the following procedure.

0.1 ml of urease was added to 20 ml of buffer solution to obtain enzymatic buffer solution. The solution was put into two test tubes respectively; 0.02 ml of a serum sample to be tested was added in one tube, while 0.02 ml of reference solution (containing urea-N 60mg/100 ml) as control was added to the other tube. The two test tubes were incubated at 37° C. for 15 minutes. Then 2 ml of color-forming solution was added into each test tube and incubated again at 37° C. for 5 minutes. The absorbance was measured at 570 nm to determine the amount of BUN.

(2) Measurement of Creatinine

Creatinine value was measured using the creatinine measurement kit (Youngdong, Pharm. Co. Ltd., Korea) in the following procedure.

4 ml of tungsten solution was added in 0.5 ml of serum sample to be tested, and stirred vigorously and then left for 10 minutes. Then the supernatant. Every 3 ml of the supernatant, reference solution of creatinine and distilled water (for blank test) was put to the separate test tubes, followed by the addition of picrate solution (1 ml each). Then 0.5 ml of 1.4N NaOH was added in each tube and stirred to measure the absorbance at 515 nm exactly after the correct lapse of 15 minutes.

(3) Measurement of sGPT sGPT value was measured using the sGPT measurement kit (Youngdong Pharm. Co. Ltd., Korea) in the following procedure.

GPT substrate solution (1 ml each) was incubated at 37° C. for 3 minutes. 0.2 ml of serum sample was added to the substrate solution and incubated again at 37° C. for 30 minutes. 1 ml of 2,4-dinitrophenol was added into the cultured solution, left for 20 minutes, then 0.4N NaOH (10 ml) is added and stirred well. The absorbance was measured at 505 nm.

(4) Urinary Test

The urinary test was performed using urine test strips (Gen 9, Youngdong Pharm. Co. Ltd., Korea) in the following procedure.

Immediately after collecting the urine from rats, the test strips were stained with the urine was used for observing the color within 1 minute.

A total of 10 male SD rats (body weight: 200 g) were used for this experiment. The animals were,weighed and then divided into two groups each containing 4 rats, and the two remaining rats were used as a control group (wherein cisplatin only was intraperitoneally administered at a dose of 5.8 mg/kg) and as a normal group (wherein no drugs were administered). To the first group (pre-treated group) decursin was administered intraperitoneally three times at a dose of 17.4 mg/kg in the molar ratio of decursin to cisplatin (3:1) at intervals of 1 hour, 24 hours and 48 hours prior to the intraperitoneal administration of cisplatin (5.8 mg/kg). To the second group (post-treatment group), decursin was administered intraperitoneally three times at a dose of 17.4 mg/kg in the molar ration of decursin to cisplatin (3:1) at intervals of 1 hour, 24 hours and 48 hours after the intraperitoneal administration of cisplatin (5.8 mg/kg). The animals were sacrificed and again weighed four days after treatment. Urine samples from each animal were tested to observe the nephrotoxicity induced by cisplatin. Blood samples were also taken and left to sit for 30 minutes to isolate the sera, which was used to determine BUN, creatinine and sGPT values as markers of nephrotoxicity. The results of these tests are shown in Tables 1 to 3.

TABLE 1

Measurement of GPT, BUN and creatinine

| Group | GPT | BUN | Creatinine |
|---|---|---|---|
| Pre-treated | 10.8 ± 4.9 | 17.5 ± 2.8 mg/dl | 0.74 ± 0.29 mg/dl |
| Post-treated | 19.0 ± 5.3 | 55.2 ± 2.1 mg/dl | 2.08 ± 0.52 mg/dl |
| Normal | 17 | 15.58 mg/dl | 0.19 mg/dl |
| Control | 18 | 69.50 mg/dl | 3.68 mg/dl |

As seen in Table 1, the cisplatin-treated group (control) showed severe nephrotoxicity as BUN and creatinine values as a marker of nephrotoxicity were determined to be 69.5 mg/dl and 3.68 mg/dl respectively. By contrast, in the decursin-treated group, BUN value was 17.5±2.8 mg/dl (normal value: less than 20) from the pre-treatment group, while BUN value was 55.2±2.1 mg/dl from the post-treatment group. BUN value in the pre-treatment group was completely recovered to the normal level, but significant differences in the post-treatment group were observed even though the nephrotoxicity was slightly alleviated.

Creatinine value in the pre-treatment group was 0.74±0.29 mg/dl (normal value: less than 1), showing complete recover to the normal level. By contrast, creatinine value in the post-treatment group was 2.08±0.52 mg/dl, showing the reduction of nephrotoxicity by about 40% compared with the control group receiving cisplatin.

Further, changes in sGPT value in the blood was observed to identify whether the alleviation of nephrotoxicity after the administration of decursin is owing to the transfer of cisplatin accumulation from the kidney to liver. Both of the pre-treatment and post-treatment groups showed normal levels as 10.8±4.9 and 19.0±5.3, respectively. As a result, it was revealed that there was no hepatotoxicity in the administration of cisplatin, which coincides with those published in other literatures.

TABLE 2

| | Urinary Test | | | | | | | | | |
|---|---|---|---|---|---|---|---|---|---|---|
| | Pre-treatment Group | | | | Post-treatment Group | | | | | |
| Parameter | 1 | 2 | 3 | 4 | 1 | 2 | 3 | 4 | Normal | Control |
| occult blood | + | | | + | + | + | + | ++ | | +++ |
| bilirubin | + | + | + | | + | + | + | | | + |
| urobilinogen | + | + | | | | + | + | | | + |

TABLE 2-continued

| | Urinary Test | | | | | | | | | |
|---|---|---|---|---|---|---|---|---|---|---|
| | Pre-treatment Group | | | | Post-treatment Group | | | | | |
| Parameter | 1 | 2 | 3 | 4 | 1 | 2 | 3 | 4 | Normal | Control |
| ketone | | | | | | | | | | ± |
| protein | | | | | | | | | | − |
| Nitrite | | | | | | | | + | | + |
| glucose | + | + | + | ++ | + | + | + | + | | ++ |
| pH | | | | | | | | | | |
| specific gravity | + | | + | | | | | | | +++ |

As confirmed from the above Table 2, there was a significant increase in control in terms of various parameters such as occult blood in urine, bilirubin, urobilinogen, ketone, protein, glucose and specific gravity. By contrast, the above parameters in the pre-treatment group were reduced to the normal level. However, the nephrotoxicity in the post-treatment group was alleviated depending on some parameters compared with cisplatin-treatment group.

TABLE 3

| | Body weight | | | | | | | | | |
|---|---|---|---|---|---|---|---|---|---|---|
| | Pre-treatment group | | | | Post-treatment group | | | | | |
| | 1 | 2 | 3 | 4 | 1 | 2 | 3 | 4 | Normal | Control |
| Weight (g) | 184 | 190 | 180 | 180 | 190 | 185 | 180 | 180 | 210 | 160 |

As confirmed from the above Table 3, the body weights were reduced in both of the pre-treatment and post-treatment group when rats were given decursin three times at the intervals of 1, 24 and 48 hours. However, the weight loss was smaller than in the group treated with cisplatin only.

The above results showed that when decursin was given to the rats at the intervals of 1, 24 and 48 hours prior to the treatment of cisplatin, it effectively inhibited nephrotoxicity activity without inducing any hepatotoxicity.

EXAMPLE 2

The effect of Decursin on Inhibiting Renal Failure Associated with Diabetic Complications 2 days after ICR mice were given alloxan (75 mg/kg, i.v.), their glucose levels at fasting were measured to select high-glucose mice. The high-glucose mice were divided into two groups; physiological saline solution was given to one group, while decursin was orally administered to the other group at a dose of 50 mg/kg for 10 days. The alloxan-free group was also orally given physiological saline solution for 10 days. The body weighs were checked periodically, together with urinary tests. To isolate their sera and kidney, mice were slightly anesthetized with ether and their abdomens were dissected. The blood samples were collected from heart to isolate the sera. The kidney was perfused with 0.9% NaCl and isolated after removal of the blood. Then the weight of right kidney was measured. Further, to measure the protein amount from the kidney tissues, these tissues were assayed according to the Bradford method using Bio-Rad protein assay kit in the presence of bovine serum albumin as a reference standard. To measure the MDA in the kidney tissues, 0.4 ml of 10% sodium dodecylsulfate was added to 0.5 ml of 10% kidney-tissue homogenization solution and left in water bath at 37° C. for 30 minutes; With the subsequent addition of 0.1N-HCl (2 ml) and 0.67% TBA (1 ml), the mixture was voltexed and left in boiling water bath for 30 minutes. The mixture was further cooled in ice bath for 2~3 minutes to stop the reaction. Then 2 ml of n-butanol was added to the mixture, stirred well and centrifuged at 3000 rpm for 10 minutes. The supernatant was collected to measure the absorbance at 532 nm. 10 $\mu$g/ml tetraethoxypropane (TEP) was employed as a reference standard. To measure the MDA in sera, 0.8% thiobarbituric acid (TBA) was added to 0.5 ml of sera and left in boiling water bath for 30 minutes. The mixture was further cooled in ice bath for 2~3 minutes to stop the reaction. The supernatant was collected to measure the absorbance at 532 nm. 10 $\mu$g/ml TEP was employed as a reference standard.

Mice were orally given decursin at a dose of 50 mg/kg for 10 days continuously. Then various parameters such as BUN and MDA in the blood as a marker of renal failure were measured, together with urinary test. When MDA value was measured by isolating the kidney tissues (table 4), the BUN value of single alloxan-treated group, 17.4±3.7 mg/dl was recovered to the normal level (4.8±0.6 mg/dl) by the treatment of decursin. The MDA value of single alloxan-treated group, 0.51±0.07, was reduced to 0.36±0.03 by the treatment of decursin, which was similar to a normal control group. Thus it was noted that the damage in the kidney was completely recovered. Since the reduction of both MDA values in the blood and kidney tissues may be clinically reasonable and desirable, the MDA value in the kidney tissues was measured. As a result, the MDA value in the kidney tissues of a single alloxan-treated group, 13.24±5.93, was reduced to 5.63±0.99 by the treatment of decursin, which was lower than that of normal control group (8.44±1.01). Thus it was revealed that decursin was quite effective in protecting the kidney tissues.

TABLE 4

BUN and MDA values in blood, and MDA values in renal tissue

| Group | BUN (mg/dl) | MDA (μg/ml) in blood | MDA (μg/g) in renal tissue |
|---|---|---|---|
| Normal | 5.4 ± 0.8 | 0.38 ± 0.04 | 8.44 ± 1.01 |
| alloxan | 17.4 ± 3.7 | 0.51 ± 0.07 | 13.24 ± 5.93 |
| alloxan + decursin | 4.8 ± 0.6 | 0.36 ± 0.03 | 5.63 ± 0.99 |

As confirmed from Table 5, below, urinary test showed that in the treatment of alloxan, the excreting amounts of occult blood, bilirubin, urobilinogen and glucose were significantly increased as well as the visible increase of specific gravity thereto. By contrast, all parameters were nearly normal in a decursin-treated group. The results coincided with the test result of BUN and MDA in blood. The weight loss of the alloxan-treated group was significantly reduced by decursin-treatment.

TABLE 5

Urinary test

| Category | Normal | | | | Alloxan | | | | | Alloxan + decursin | | | |
|---|---|---|---|---|---|---|---|---|---|---|---|---|---|
| | +++ | ++ | + | − | +++ | ++ | + | ± | − | +++ | ++ | + | − |
| Occult blood | | | | 10 | 8 | 2 | | | | | | 2 | 8 |
| Bilirubin | | 1 | | 9 | 2 | 6 | 2 | | | | | 2 | 8 |
| Urobilinogen | | | | 10 | | | 10 | | | | | 1 | 9 |
| Ketone | | | | 10 | | | | 3 | 7 | | | | 10 |
| Protein | | | | 10 | | | | | 10 | | | | 10 |
| Nitrite | | | | 10 | | | 4 | | 6 | | | | 10 |
| Glucose | | | | 9 | | 10 | | | | | | 1 | 9 |
| pH | | | | 10 | | | | | 10 | | | | 10 |
| Specific gravity | | | | 10 | 9 | 1 | | | | | | | 10 |

EXAMPLE 3

The Cell Differentiation Induction Activity of Decursin

U-937 cells, optioned from Korea Cell Line Bank, was cultured in RPMI 1640 medium (Sigma Co., R-6504) supplemented with 10% fetal bovine serum (FBS). The medium was exchanged every 5 day by 70%. U-937 cells were inoculated into a cell culture dish at concentration of $2 \times 10^5$ cells/ml. Then decursin added into the dish at concentration of $10^{-8} \sim 10^{-6}$M, then the cells were cultured for 4 days. Trypan blue exclusion test was performed to determine the number of live cells using a hemacytometer, and the percentage of cancer-cell growth inhibition was calculated. Then, the differentiation was induced by treating with $10^{-2}$M diluted ethanol solution containing various amount of decursin in the medium.

U-937 cells were plated on a cell culture dish at a concentration of $2 \times 10^5$ cells/ml in a medium containing $10^{-7}$M decursin and incubated in a 5% $CO_2$ incubator at 37° C.

In the nitrobluetetrazolium (NBT) reduction test, cell solution (about $1 \times 10^6$ cells/ml) was well stirred and pelleted by centrifugation at 2000 rpm for 5 minutes. The pellets were suspended in 0.5 ml of medium, followed by the addition of a mixing solution (0.5 ml) containing $10^{-6}$M formyl-methionine leucine phenylalanine (fMLP) and NBT 1.0 mg/DPBSml (1:9). The mixture was incubated at 37° C. for 30 minutes. The reaction was stopped in ice bath and centrifuged at 2000 rpm for 5 minutes. The supernatant was removed and then 200 μl of DPBS was added. The solution was lightly swayed and checked under a microscope to observe a minimum number of 200 cells. The number of NBT (+) cells was calculated by percentage.

In the phagocytosis test, $10^6$ cells were well stirred and pelleted by centrifugation at 2000 rpm for 5 minutes. 1 ml of 0.2% serum free medium solution in polystyrene particle were added to the pellets, swayed and incubated at 37° C. for 4 hours. After being washed with phosphate buffered saline (PBS) three times, cell pellets were harvested and then about 200 μl of DPBS was added. The solution was lightly swayed and checked under a microscope to observe a minimum number of 200 cells. The number of cells containing the particles was calculated by percentage.

To determine α-naphthyl acetate esterase activity in the esterase activity test, the cultured solution of U-937 cells was pelleted by centrifugation at 2000 rpm for 5 minutes, followed by the addition of 100 μl PBS to prepare a cell-concentrated solution. A drop of the cell solution was put on a slide glass and dried for more than 1 hour. Then 40 ml of deionized water was preheated at 37° C. 1 ml of sodium nitrate solution was mixed with 1 ml of Fast Blue BB base solution and left for 2 minutes. The mixture, being turned to yellow color with thick brown, was added to 40 ml of the preheated deionized water. After the addition of 5 ml of TRIZMAL TM 7.6 buffer solution (Sigma Co. 870-2) and 1 ml of α-naphthyl acetate solution, the resulting solution, which was turned to green color, was poured into a petri dish. The cells on a slide glass were fixed with citrate-acetone-formaldehyde solution (CAF solution) at room temperature. The cells were soaked in the previously prepared solution and incubated at 37° C. for 30 minutes at a dark place. The cells were completely washed with deionized water for more than 2 minutes and counterstained with hematoxylin solution for 2 minutes, washed with tap water and dried in the air. After completely dried, the cells were observed under a microscope to determine the blackish cell numbers.

To determine naphthol AS-D chloroacetate esterase activity, the cultured solution of U-937 cells was pelleted by centrifugation at 2000 rpm for 5 minutes, followed by the addition of 100 μl PBS to prepare a cell-concentrated solution. A drop of the cell solution was put on a slide glass and dried for more than 1 hour. Then 40 ml of deionized water was preheated at 37° C. 1 ml of sodium nitrate solution was mixed with 1 ml of Fast Red Violet LB base solution and left for 2 minutes. The mixture was added to 40 ml of preheated deionized water. After the addition of 5 ml of TRIZMAL TM 6.3) buffer solution (Sigma Co. T-3128) and 1 ml of naphthol AS-D chloroacetate solution, the resulting solution, which was turned to red color was poured on a petri dish. The cells on a slide glass were fixed with citrate-acetone-formaldehyde solution, (CAF solution) at room temperature. The cells were soaked in the previously prepared solution and incubated at 37° C. for 30 minutes at a dark place. The cells were completely washed with deionized water for more than 2 minutes and counterstained with hematoxylin solution for 2 minutes, washed with tap water and dried in the air. After completely dried, the cells were observed under a microscope to calculate the reddish cell numbers by percentage.

(1) Growth Inhibition Test

As confirmed from the following Table 6, when measuring the growth inhibition rate of decursin on U-937 cells after 96 hours, decursin showed 30–50% of inhibitory effect at a concentration of $10^{-8} \sim 10^{-6}$M.

TABLE 6

Growth inhibition test

| Conc. | Growth inhibition rate (%) | |
|---|---|---|
| | Vitamin $D_3$ | Decursin |
| $1 \times 10^{-6}$M | 54.0 ± 6.7 | 52.0 ± 2.8 |
| $5 \times 10^{-7}$M | 48.0 ± 6.0 | 48.0 ± 7.1 |
| $1 \times 10^{-7}$M | 42.5 ± 6.4 | 42.0 ± 6.4 |
| $5 \times 10^{-8}$M | 33.5 ± 0.7 | 35.5 ± 7.4 |
| $1 \times 10^{-8}$M | 26.0 ± 5.7 | 31.0 ± 7.8 |

(2) NBT Reduction Test

The differentiation was investigated by using the fact that the differentiated leukocyte cells may generate superoxide anion by stimulation. The cells were treated with decursin or vitamin $D_3$ at $10^{-7}$M and incubated for 4 days. The cultured mixture, which was reacted with superoxide, was reduced to form a precipitate. Then NBT was added to the precipitate (Table 7). As confirmed from the following, Table 7, 14% of positive cells showed NBT reduction power in control, while positive cells treated with vitamin $D_3$ at $10^{-7}$M and decursin at the same concentration were increased by 39% and 43%, respectively.

TABLE 7

NBT reduction test

| Conc. | Untreated | Decursin | Vitamin $D_3$ |
|---|---|---|---|
| $1 \times 10^{-7}$M | 14.2 ± 2.1% | 43.1 ± 4.0% | 39.0 ± 2.1% |

(3) Phagocytosis Test

U-937 cells were treated with decursin or vitamin $D_3$ at $10^{-7}$M, and then incubated for 4 days. The results of phagocytosis test designed to assess the functional change according to differentiation of U-937 cells was shown in the following Table 8. As confirmed from the following Table 8, about 5% of control cells showed the phagocytosis activity, while cells treated with vitamin $D_3$ and decursin at the same concentration were increased by 25.8% and 28.6%, respectively.

TABLE 8

Phagocytosis test

| Conc. | Untreated | Decursin | Vitamin $D_3$ |
|---|---|---|---|
| $1 \times 10^{-7}$M | 4.8 ± 0.8% | 28.6 ± 1.2% | 25.8 ± 1.3% |

(4) Esterase Activity Test

Table 9 showed an enzyme activity test results of naphthol AS-D chloroacetate esterase that is developed via differentiation into granulocyte like cells and α-naphtyl acetate esterase which is developed via differentiation into macrophage like cells. As confirmed from Table 9, none of the cells showed naphtol AS-D chloroacetate esterase activity in all drugs. However, about 10% of cells showed α-naphtylacetate esterase activity in control cells, while it demonstrated that 80% in vitamin $D_3$-treated group and 83% in decursin-treated group showed α-naphtylacetate esterase activity. Thus it was considered that the cells were differentiated into macrophage.like cells by the action of decursin.

TABLE 9

Esterase activity test

| | Activity (%) | | |
|---|---|---|---|
| Enzyme | Control | Vitamin $D_3$ | Decursin |
| α-Naphtylacetate esterase | 10.5 ± 0.7 | 79.3 ± 4.5 | 83.3 ± 3.0 |
| Naphtol AS-D chloroacetate esterase | 0.0 | 0.0 | 0.0 |

From the above results, it was confirmed that decursin is effective in inducing cancer-cell differentiation. More specifically, as a result of determining the cytotoxicity of decursin and Vitamin $D_3$ at a concentration of $10^{-8}$M~$10^{-6}$M on human-derived U-937 cells, U-937 cells exhibited a very high cytotoxicity. To investigate the differentiation-inducing activity of decursin on U-937 cells at $10^{-7}$M, which showed about 33% of cytotoxicity, the cells were treated with decursin for 4 days, with Vitamin $D^3$ as comparative material. After performing NBT reduction test and phagocytosis test, decursin at $10^{-7}$M showed more potent differentiation power than Vitamin $D_3$ in both the reduction test and phagocytosis test and the cells were differentiated into macrophage like cells. Therefore, it was confirmed that decursin effectively induces cancer-cell differentiation.

EXAMPLE 4

The Toxicity Test of Decursin on Normal Cells

To determine the cytotoxicity of decursin on normal cells, they were sub-cultured in a medium-199 containing, 3% fetal bovine serum (FBS), penicillin (100 U/ml) and streptomycin (100 µg/ml) every 3 to 4 day. Then cells were treated with trypsin to prepare a cell suspension. 1 ml of the cell suspension was seeded on 24-well plate at a concentration of $2 \times 10^5$ in cells/ml an d attached to the medium for one day. After the supernatant was removed, 1 ml of decursin was added to the cell culture medium at appropriate concentrations and incubated for 3 days to count the cell numbers. The results were shown in the following Table 10. As confirmed in Table 10, the cytotoxicity on normal cells (LLC-PK1) was not shown down to $10^{-6}$M.

TABLE 10

Cytotoxicity test on normal cells

| Conc. | Growth inhibition rate (%) | |
|---|---|---|
| | Vitamin $D_3$ | Decursin |
| $1 \times 10^{-6}$M | 9.0 ± 0.7 | 0.0 ± 0.0 |
| $5 \times 10^{-7}$M | 4.0 ± 0.1 | 0.0 ± 0.0 |
| $1 \times 10^{-7}$M | 4.0 ± 0.2 | 0.0 ± 0.0 |

TABLE 10-continued

Cytotoxicity test on normal cells

| Conc. | Growth inhibition rate (%) | |
|---|---|---|
| | Vitamin $D_3$ | Decursin |
| $5 \times 10^{-8}$M | 0.0 ± 0.0 | 0.0 ± 0.0 |
| $1 \times 10^{-8}$M | 0.0 ± 0.0 | 0.0 ± 0.0 |

As described above, decursin is an effective nephrotoxicity inhibitor to alleviate the nephrotoxicity. Especially, decursin can be effectively used in the antineoplastic composition or antidiabetic composition. In addition, decursin can be used as a cancer-cell differentiation induction agent to effectively induce cancer-cell differentiation, especially as a human leukemia-cell differentiation induction agent to cure human leukemia.

What is claimed is:

1. A pharmaceutical composition decursin, an anti-diabetic agent and a pharmaceutically acceptable carrier.

2. The pharmaceutical composition according to claim 1, wherein the molar ratio of decursin to the anti-diabetic agent is about 0.2–10:1.

3. A method of inhibiting nephrotoxicity in a mammal, comprising administering to a mammal in need thereof, a therapeutically effective amount of a composition comprising decursin and a pharmaceutically acceptable carrier.

4. The method according to claim 3, wherein the therapeutically effective amount comprises a dose of about 1 to 500 mg decursin per kg of body weight of the mammal.

5. A method of inducing the differentiation of cancer cells in a mammal, said method comprising administering to a mammal in need thereof, a therapeutically effective amount of a composition comprising decursin and a pharmaceutically acceptable carrier.

6. The method according to claim 5, wherein the mammal is a human and the cancer cells are human leukemia cells.

7. The method according to claim 5, wherein the therapeutically effective amount comprises a dose of about 1 to 300 mg decursin per kg of body weight of the mammal.

8. A method of reducing the nephrotoxicity of an anti-neoplastic agent in a mammal, said method comprising administering to a mammal being treated with a first anti-neoplastic agent, a therapeutically effective amount of a composition comprising decursin and a pharmaceutically acceptable carrier.

9. The method according to claim 8, wherein the molar ratio of decursin to the first anti-neoplastic agent is about 1–5:1.

10. The method according to claim 8, wherein the first anti-neoplastic agent is cisplatin.

11. A method of reducing the nephrotoxicity of an anti-diabetic agent in a mammal, said method comprising administering to a mammal receiving said anti-diabetic agent, a therapeutically effective amount of a composition comprising decursin and a pharmaceutically acceptable carrier.

* * * * *

UNITED STATES PATENT AND TRADEMARK OFFICE
CERTIFICATE OF CORRECTION

PATENT NO. : 6,525,089 B1 Page 1 of 1
DATED : February 25, 2003
INVENTOR(S) : Chong et al.

It is certified that error appears in the above-identified patent and that said Letters Patent is hereby corrected as shown below:

<u>Title page,</u>
Item [73], Assignee, delete "Binex Co., Ltd. (KR)" and insert
-- Binex Co., Ltd. (KR), Chong, SE Young (KR) and Kim, IK Hwan (KR) --

<u>Column 13,</u>
Line 20, insert the word -- comprising -- after the word "composition"

Signed and Sealed this

Thirteenth Day of January, 2004

JON W. DUDAS
*Acting Director of the United States Patent and Trademark Office*